US012702463B2

(12) United States Patent
Matsuo et al.

(10) Patent No.: US 12,702,463 B2
(45) Date of Patent: Aug. 11, 2026

(54) TREATMENT DEVICE FOR ABLATION

(71) Applicant: OLYMPUS MEDICAL SYSTEMS CORP., Tokyo (JP)

(72) Inventors: Nobuko Matsuo, Hachioji (JP); Kunihide Kaji, Hachioji (JP); Yoshisane Nakamura, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 832 days.

(21) Appl. No.: 17/568,076

(22) Filed: Jan. 4, 2022

(65) Prior Publication Data

US 2022/0273351 A1 Sep. 1, 2022

Related U.S. Application Data

(60) Provisional application No. 63/154,841, filed on Mar. 1, 2021, provisional application No. 63/154,854, filed (Continued)

(51) Int. Cl.
*A61B 18/04* (2006.01)
*A61B 18/00* (2006.01)

(52) U.S. Cl.
CPC .. *A61B 18/042* (2013.01); *A61B 2018/00494* (2013.01); *A61B 2018/00577* (2013.01); *A61B 2018/00982* (2013.01)

(58) Field of Classification Search
CPC ........ A61B 18/042; A61B 2018/00494; A61B 2018/00577; A61B 2018/00982; A61B 2018/0072; A61B 2018/00744
See application file for complete search history.

(56) References Cited

U.S. PATENT DOCUMENTS 5,087,478 A * 2/1992 Williamson ........ C23C 14/0611 118/723 VE
5,720,745 A * 2/1998 Farin .................... A61B 18/042 606/49

(Continued)

FOREIGN PATENT DOCUMENTS

JP 2002-301088 A 10/2002
WO 2019/199281 A1 10/2019
WO 2021/140609 A1 7/2021

OTHER PUBLICATIONS

International Search Report dated Mar. 29, 2022, issued in corresponding International Patent Application No. PCT/JP2022/003547.

*Primary Examiner* — Linda C Dvorak
*Assistant Examiner* — Lindsay Regan Lancaster
(74) *Attorney, Agent, or Firm* — Morgan, Lewis & Bockius LLP

(57) ABSTRACT

An ablation treatment device for ablating treatment procedure used with endoscope device is disclosed. The ablation treatment device is inserted through the endoscope device and protruded into the human body, where the equipped neutral electrode and a gas channel for injecting inert gas is protruded. Together with another gas channel formed on the endoscope device, two types of gases are injected into the human body together with application of high frequency currents to perform ablation procedure. The ablation treatment device is controlled through a control circuit that administers control of the injection of the gases and application of high frequency currents.

28 Claims, 12 Drawing Sheets

Related U.S. Application Data on Mar. 1, 2021, provisional application No. 63/154,856, filed on Mar. 1, 2021, provisional application No. 63/154,857, filed on Mar. 1, 2021, provisional application No. 63/154,847, filed on Mar. 1, 2021.

(56) References Cited

U.S. PATENT DOCUMENTS 9,288,886 B2 * 3/2016 Koo .................. H01J 37/32348
9,592,070 B2 3/2017 Inoue
2005/0118350 A1 * 6/2005 Koulik ..................... H05H 1/44 219/121.36
2008/0097425 A1 * 4/2008 Truckai ................ A61B 18/042 606/41
2009/0024122 A1 * 1/2009 Fischer ................ A61B 18/042 600/104
2009/0053901 A1 * 2/2009 Goto ......................... C01B 3/00 257/E21.256
2012/0041437 A1 * 2/2012 Truckai ................ A61B 18/042 606/41
2012/0172874 A1 * 7/2012 Fischer ................ A61B 18/042 606/49
2015/0038790 A1 * 2/2015 Rontal ................. A61B 1/0051 604/20
2018/0085155 A1 3/2018 Konesky et al.
2020/0261069 A1 8/2020 Inoue et al.

* cited by examiner

Control Sequence for Commencing the Ablation Treatment Procedure

| Seq. No. | 1st Step | 2nd Step | 3rd Step |
|---|---|---|---|
| 1 | CO2 | Inert Gas | HF |
| 2 | CO2 | HF | Inert Gas |
| 3 | CO2 | Inert Gas/HF | |
| 4 | CO2/Inert Gas | HF | |
| 5 | CO2/HF | Inert Gas | |
| 6 | CO2/Inert Gas/HF | | |
| 7 | Inert Gas | CO2 | HF |
| 8 | Inert Gas | HF | CO2 |
| 9 | Inert Gas | CO2/HF | |
| 10 | Inert Gas/HF | CO2 | |
| 11 | HF | CO2 | Inert Gas |
| 12 | HF | Inert Gas | CO2 |
| 13 | HF | CO2/Inert Gas | |

FIG. 8

Control Sequence for Halting the Ablation Treatment Procedure

| Seq. No. | 1st Step | 2nd Step | 3rd Step |
|---|---|---|---|
| 14 | CO2 | Inert Gas | HF |
| 15 | CO2 | HF | Inert Gas |
| 16 | CO2 | Inert Gas/HF | |
| 17 | CO2/Inert Gas | HF | |
| 18 | CO2/HF | Inert Gas | |
| 19 | CO2/Inert Gas/HF | | |
| 20 | Inert Gas | CO2 | HF |
| 21 | Inert Gas | HF | CO2 |
| 22 | Inert Gas | CO2/HF | |
| 23 | Inert Gas/HF | CO2 | |
| 24 | HF | CO2 | Inert Gas |
| 25 | HF | Inert Gas | CO2 |
| 26 | HF | CO2/Inert Gas | |

FIG. 9

Control Sequence for Commencing the Ablation Treatment Procedure

| Seq. No. | 1st Step | 2nd Step | 3rd Step |
|---|---|---|---|
| 1A | CO2 | Inert Gas | HF |
| 2A | CO2 | HF | Inert Gas |
| 3A | CO2 | Inert Gas/HF | |
| 4A | CO2/Inert Gas | HF | |
| 5A | CO2/HF | Inert Gas | |
| 6A | CO2/Inert Gas/HF | | |
| 7A | Inert Gas | CO2 | HF |
| 8A | Inert Gas | CO2/HF | |
| 9A | HF | CO2 | Inert Gas |
| 10A | HF | CO2/Inert Gas | |

FIG. 10

Control Sequence for Commencing the Ablation Treatment Procedure

| Seq. No. | 1st Step | 2nd Step | 3rd Step |
|---|---|---|---|
| 1B | Inert Gas | HF | CO2 |
| 2B | Inert Gas/HF | CO2 | |
| 3B | HF | Inert Gas | CO2 |

FIG. 11

Control Sequence for Halting the Ablation Treatment Procedure

| Seq. No. | 1st Step | 2nd Step | 3rd Step |
|---|---|---|---|
| 1C | CO2/Inert Gas | HF | |
| 2C | CO2/HF | Inert Gas | |
| 3C | CO2/Inert Gas/HF | | |
| 4C | Inert Gas | CO2 | HF |
| 5C | Inert Gas | HF | CO2 |
| 6C | Inert Gas | CO2/HF | |
| 7C | Inert Gas/HF | CO2 | |
| 8C | HF | CO2 | Inert Gas |
| 9C | HF | Inert Gas | CO2 |
| 10C | HF | CO2/Inert Gas | |

FIG. 12

Control Sequence for Halting the Ablation Treatment Procedure

| Seq. No. | 1st Step | 2nd Step | 3rd Step |
|---|---|---|---|
| 1D | CO2 | Inert Gas | HF |
| 2D | CO2 | HF | Inert Gas |
| 3D | CO2 | Inert Gas/HF | |

FIG. 13

TREATMENT DEVICE FOR ABLATION

RELATED APPLICATION DATA

This application is based on and claims priority under 35 U.S.C. § 119 to U.S. Provisional Application Nos. 63/154,841; 63/154,847; 63/154,854; 63/154,856; and 63/154,857, each of which was filed on Mar. 1, 2021. The entire contents of each of these applications are incorporated herein by reference.

FIELD OF DISCLOSURE

The present invention relates to a treatment device used for ablation procedure. In particular, the disclosure relates to treatment devices for radiofrequency ablation in which a gas is emitted from the treatment device and forms discharging atmosphere for the ablation procedure, particular for treating gastroesophageal reflux disease.

BACKGROUND

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art against the present invention.

Gastroesophageal reflux disease is caused when contents of the stomach, mainly gastric acid, move backward into the esophagus causing unpleasant subjective symptoms such as heart burn or hyperacidity, and is an inflammatory disease of the esophagus causing pathological conditions such as esophagitis, Barrett's esophagus, or esophageal adenocarcinoma resulting from Barrett's esophagus.

Reflux of the gastric acid into the esophagus often occurs when the cardia is relaxed or an abdominal pressure increases. When there is a sliding esophageal hiatal hernia, since clamping of the cardia by the diaphragm is insufficient, reflux of the gastric acid into the esophagus is likely to occur.

In order to prevent the reflux of the gastric acid into the esophagus to occur, a medical procedure generally referred to as Anti-Reflux MucoSectomy (ARMS) was developed. In this medical procedure, the mucous membrane in the vicinity of the gastroesophageal junction is resected to cause scarring at the resected site, which would eventually form an incomplete cicatricial stenosis. The incomplete cicatricial stenosis in either or both of the esophagus and the stomach forms an opening capable of reducing dysphagia occurring when food passes and preventing gastric acid from refluxing, thereby preventing the gastric acid from reaching the esophagus. Examples of such medical procedure are disclosed in U.S. Pat. No. 9,592,070 entitled METHOD FOR TREATING GASTROESOPHAGEAL REFLUX DISEASE, the entire disclosure of which is hereby incorporated by reference herein.

Another type of medical procedure generally referred to as anti-reflux mucosal ablation (ARMA) is an endoscopic treatment method in which the mucous membrane is damaged by ablating the mucous membrane basal cell beneath the mucous layer and an incomplete cicatricial stenosis is formed in the digestive tract through the restoration of the damaged area. Examples of such medical procedure are disclosed in U.S. Pat. Pub. No. 2020/0261069A1 entitled METHOD FOR TREATING GASTROESOPHAGEAL REFLUX DISEASE, the entire disclosure of which is hereby incorporated by reference herein.

An example endoscopic-surgery apparatus for Argon-plasma coagulation (APC) is disclosed in U.S. Pat. Pub. No. 2009/0024122A1. The related art endoscopic-surgery apparatus instrument 10 is disclosed with a probe 11 that is constructed as a probe for Argon-plasma coagulation (APC). By way of an endoscope 80, the probe 11 has been guided to a tissue 99 to be treated, in this case in the region of the vocal folds of a patient. The probe 11 comprises a first working channel 14 for the Argon-plasma coagulation and a second working channel 15 disposed coaxially thereto. At the distal end of each of the channels 14 and 15 is an outlet opening 14*a* or 15*a*, respectively. An electrode 50 supplies a high-frequency current to a distal end 12 of the probe 11, and thus to the tissue 99 that is to be treated. The electrode 50 is disposed within the first working channel 14. The electrode 50 is connected by way of current-delivery devices 51 to an HF generator 90 for producing a high-frequency voltage. During the APC, an inert gas 60, preferably Argon, flows around the electrode 50 so that, due to an interaction between the HF current and the gas, a plasma 61 is produced. Within the probe 11, the electrode 50 opens into a nozzle device 40*b*, so as to obtain a plasma stream 61 that is as well targeted as possible. By way of the plasma stream 61, the HF current can be guided to the tissue 99, so that the tissue 99 is coagulated.

By way of the second channel 15, which is disposed coaxially with respect to the first channel 14, another gas flow 70 may be directed to the operation region. This can occur prior to ionization or during the Argon-plasma coagulation. This gas flow 70, preferably a current of Argon gas, encloses the plasma stream 61 so that an envelope 71 of inert gas is built up by the protective flow 70 in the immediate surroundings of the plasma stream 61. That is, the ionizable gas fills not only in the space between the outlet opening of the probe and the tissue to be treated, as would be the case for example with a single-lumen probe; but also, it fills a larger volume, through which the coagulation current can find its way. The gas envelope 71 acts as a protective atmosphere, displacing reactive gases such as oxygen or carbon monoxide from the operation region, so that ignition of these gases in association with the plasma stream 61, which would be dangerous to the patient, is prevented.

The outlet opening 15*a* of the second channel 15 is disposed, with reference to an axial direction S of extent of the probe 11, towards the distal end 12 of the probe 11 and before the outlet opening 14*a* of the first channel 14. That is, the first channel 14 projects out of the second channel 15. Thus, the protective atmosphere 71 can be built up with extreme reliability, because it is ensured that the distal end of the first channel 14 and hence the plasma stream 61 are situated completely within the protective atmosphere 71.

Because the second channel 15 for supplying additional Argon gas to the operation region is disposed within the APC probe 11, the formation of the Argon cloud that envelops the plasma stream 61, i.e. the protective atmosphere 71, is independent of the position of the probe 11 in relation to the endoscope 80. Furthermore, the additional Argon flow can be arbitrarily turned on and off, depending on the extent to which the protective flow 70 is desired.

A drawback of the related art treatment device is the complexity of the structure of probe 11. In addition to the electrode 50 for supplying high frequency currents, the first working channel 14 and the second working channel 15 need to be configured with sufficient width for allowing the inert gas 60 and the gas flow 70 to flow therethrough, causing issues for minimizing the overall size of the probe 11. The related art treatment device also does not disclose how the application of high frequency electricity, injection of inert gas 60, and injection of gas flow 70 are controlled.

SUMMARY

Accordingly, there is a need for designing a treatment device used for ablation procedures with an efficient structure in view of the practical usage, which would substantially obviate one or more of the issues due to limitations and disadvantages of related art treatment devices. An object of the present disclosure is to provide an improved treatment device having an efficient structure and practical administration of the associated medical procedure. At least one or some of the objectives is achieved by the treatment device disclosed herein.

Additional features and advantages will be set forth in the description that follows, and in part will be apparent from the description, or may be learned by practice of the invention. The objectives and other advantages of the disclosed treatment device will be realized and attained by the structure particularly pointed out in the written description and claims thereof, as well as the appended drawings.

In general, the disclosed structures and methods provide for an endoscopic treatment device which emits from an end both an inert gas, such as Ar, as well a gas having a lower dischargeability than Ar. This lower dischargeability gas, such as carbon dioxide, displaces some of the volume of Ar, particularly in the vicinity of the end cap of the endoscopic treatment device, resulting discharging to Argon gas being reduced during the ablation procedure. Various structures and methods are disclosed to implement the targeted delivery of the lower dischargeability gas in combination with Argon gas. For example, the lower dischargeability gas can be emitted from between the APC probe and a channel through the endoscope, or from a nozzle for air/water flow on the distal end of endoscope.

Embodiments of the disclosed endoscope system comprises an endoscope including an insertion channel, a treatment tube inserted through and protruding out from the distal end of the insertion channel, wherein the treatment tube includes an electrode and a first gas channel, a first gas source configured to supply a first gas through the first gas channel, a second gas source configured to supply a second gas through a second gas channel that is not included within a treatment tube and supplies the second gas in the direction of the distal end of the insertion channel, an electricity power source configured to supply a first high frequency current to the electrode sufficient to ionize the first gas into a plasma state, and a control circuit controlling the electricity power source, the first gas source, and the second gas source. In various embodiments, the control circuit is programmed to supply the second gas prior to, simultaneously with, or after supplying the first gas; to supply the second gas prior to, simultaneously with, or after applying the first high frequency current; or in various combinations thereof. The first gas ionizes into the plasma state at the first high frequency amperage, the second gas ionizes into a plasma state at a second high frequency amperage, and the second high frequency current is higher than the first high frequency amperage.

In another aspect of the present disclosure, the first gas is an inert gas, such as Argon.

In another aspect of the present disclosure, the second gas is carbon dioxide.

In another aspect of the present disclosure, the first gas is Argon and the second gas is carbon dioxide, and the first high frequency current is sufficient to ionize Argon into the plasma state but not sufficient to ionize the carbon dioxide into the plasma state.

In another aspect of the present disclosure, a plenum between an outer surface of a wall of the electrode and an inner surface of the wall of the treatment tube forms the first gas channel.

In another aspect of the present disclosure, the first gas channel extends through the body of the electrode and includes an opening on a distal face surface of the electrode.

In another aspect of the present disclosure, a plenum between an outer surface of a wall of the treatment tube and an inner surface of the wall of the insertion channel forms the second gas channel.

In another aspect of the present disclosure, a third gas source configured to supply a third gas through a third gas channel, wherein the third gas channel is formed within the endoscope and is separate from the insertion channel, and wherein the third gas channel has an opening in the distal end of the endoscope that is spaced apart from an opening for the treatment tube in the distal end of the endoscope.

In another aspect of the present disclosure, the second gas channel is formed within the endoscope and is separate from the insertion channel, and wherein the second gas channel has an opening in the distal end of the endoscope that is spaced apart from an opening for the treatment tube in the distal end of the endoscope.

In another aspect of the present disclosure, the treatment tube includes an outer portion and an inner portion, the outer portion having a larger diameter compared to the inner portion and the diameter of the outer portion is equal to or slightly smaller than the inner diameter of the insertion channel.

In another aspect of the present disclosure, the outer portion extends more than 10 mm from the distal end of the treatment tube, not considering the electrode.

In another aspect of the present disclosure, a cap is attached at the distal end of the endoscope.

In another aspect of the present disclosure, the outer portion and the electrode both protrude out from an area covered by the cap.

In another aspect of the present disclosure, the electrode is a neutral electrode.

In another aspect of the present disclosure, the outer surface of the wall of the treatment tube includes one or more recesses.

In another aspect of the present disclosure, the recess is triangular shaped, curve-shaped, curb-shaped, or block-shaped.

In another aspect of the present disclosure, the outer surface of the wall of the treatment tube includes one or more flat surfaces.

In another aspect of the present disclosure, a control device comprises a controller including a control circuit for controlling a first gas source, a second gas source, and an electricity power source. The first gas source is configured to supply a first gas through the first gas channel within an endoscope, the second gas source is configured to supply a second gas through a second gas channel within an endoscope, and the electricity power source is configured to supply a first high frequency current to the electrode sufficient to ionize the first gas into a plasma state. The first gas ionizes into the plasma state at the first high frequency amperage, the second gas ionizes into a plasma state at a second high frequency amperage, and the second high frequency current is higher than the first high frequency amperage.

In another aspect of the present disclosure, the control circuit is programmed to supply the second gas prior to or simultaneously with supplying the first gas or to supply the second gas prior to or simultaneously with applying the first high frequency current.

In another aspect of the present disclosure, the control circuit is programmed to supply the second gas after supplying the first gas and the applying the first high frequency current.

In another aspect of the present disclosure, the control circuit is programmed to stop the supply of the second gas prior to stopping the supply of the first gas or stopping the application of the first high frequency current.

In another aspect of the present disclosure, the control circuit is programmed to stop the supply of the second gas after stopping the supply of the first gas or stopping the application of the first high frequency current.

In another aspect of the present disclosure, the control circuit is programmed to supply the second gas prior to supplying the first gas and applying the first high frequency current simultaneously.

In another aspect of the present disclosure, the control circuit is programmed to supply the first and second gas simultaneously and prior to applying the first high frequency current.

In another aspect of the present disclosure, the control circuit is programmed to supply the second gas and apply the first high frequency current simultaneously and prior to supplying the first gas.

In another aspect of the present disclosure, the control circuit is programmed to supply the first and second gas and apply the first high frequency current simultaneously.

In another aspect of the present disclosure, the control circuit is programmed to supply the first gas prior to supplying the second gas and supply the second gas prior to applying the first high frequency current.

In another aspect of the present disclosure, the control circuit is programmed to supply the first gas prior to applying the first high frequency current and supplying the second gas simultaneously.

In another aspect of the present disclosure, the control circuit is programmed to apply the first high frequency current prior to supplying the second gas and supply the second gas prior to supplying the first gas.

In another aspect of the present disclosure, the control circuit is programmed to apply the first high frequency current prior to supplying the first and second gas simultaneously.

In another aspect of the present disclosure, the control circuit is programmed to supply the second gas prior to or simultaneously with supplying the first gas or supply the second gas prior to or simultaneously with applying the first high frequency current.

In another aspect of the present disclosure, the control circuit is programmed to supply the second gas after supplying the first gas and the applying the first high frequency current.

In another aspect of the present disclosure, the control circuit is programmed to stop the supply of the second gas prior to stopping the supply of the first gas or stopping the application of the first high frequency current.

In another aspect of the present disclosure, the control circuit is programmed to stop the supply of the second gas after stopping the supply of the first gas or stopping the application of the first high frequency current.

In another aspect of the present disclosure, the control circuit is programmed to supply the first gas prior to applying the first high frequency current and to supply the first high frequency current prior to supplying the second gas.

In another aspect of the present disclosure, the control circuit is programmed to supply the first gas and apply the first high frequency current simultaneously and prior to supplying the second gas.

In another aspect of the present disclosure, the control circuit is programmed to apply the first high frequency current prior to supplying the first gas and to supply the first gas prior to supplying the second gas.

In another aspect of the present disclosure, the control circuit is programmed to stop the supply of the second gas prior to stopping the supply of the first gas and stop the supply of the first gas prior to stop the application of the first high frequency current.

In another aspect of the present disclosure, the control circuit is programmed to stop the supply of the second gas prior to stopping the application of the first high frequency current and stop the application of the first high frequency current prior to stopping the supply of the first gas.

In another aspect of the present disclosure, the control circuit is programmed to stop the supply of second gas prior to simultaneously stopping the supply of the first gas and the application of the first high frequency current.

In another aspect of the present disclosure, the control circuit is programmed to simultaneously stop the supply of the first and second gas prior to stopping the application of the first high frequency current.

In another aspect of the present disclosure, the control circuit is programmed to simultaneously stop the supply of the second gas and application of the first high frequency current prior to stopping the supply of the first gas.

In another aspect of the present disclosure, the control circuit is programmed to simultaneously stop the supply of the first and second gas and application of the first high frequency current.

In another aspect of the present disclosure, the control circuit is programmed to stop the supply of the first gas prior to stopping the supply of the second gas and stop the supply of the first gas prior to stopping the application of the first high frequency current.

In another aspect of the present disclosure, the control circuit is programmed to stop the supply of the first gas prior to stopping the application of the first high frequency current and stop the application of the first high frequency prior to stopping the supply of the second gas.

In another aspect of the present disclosure, the control circuit is programmed to stop the supply of the first gas prior to simultaneously stopping the supply of the second gas and stopping the application of the first high frequency current.

In another aspect of the present disclosure, the control circuit is programmed to simultaneously stop the supply of the first gas and application of the first high frequency current prior to stopping the supply of the second gas.

In another aspect of the present disclosure, the control circuit is programmed to stop the application of the first high frequency current prior to stopping the supply of the second gas and stop the supply of the second gas prior to stopping the supply of the first gas.

In another aspect of the present disclosure, the control circuit is programmed to stop the application of the first high frequency current prior to stopping the supply of the first gas and stop the supply of the first gas prior to stopping the supply of the second gas.

In another aspect of the present disclosure, the control circuit is programmed to stop the application of the first high frequency current prior to simultaneously stopping the supply of the first gas and second gas.

In another aspect of the present disclosure, the control circuit is programmed to supply the second gas prior to or simultaneously with supplying the first gas or supply the second gas prior to or simultaneously with applying the first high frequency current.

In another aspect of the present disclosure, the control circuit is programmed to supply of the second gas is stopped after stopping the supply of the first gas or after stopping the application of the first high frequency current.

In another aspect of the present disclosure, a method of controlling a flow of a first gas and a second gas, a first gas source configured to supply the first gas through the first gas channel, and a second gas source configured to supply the second gas through a second gas channel is disclosed. The method comprises supplying the first gas through the first gas channel, for example, to a treatment area, aimed to reach beyond the distal end of an electrode, supplying a second gas through the second gas channel, for example, to a treatment area, not aimed to reach beyond the distal end of an electrode, and applying a first high frequency current to the electrode to ionize the first gas to a plasma state, wherein the first high frequency current is sufficient to ionize the first gas into a plasma state. The first gas ionizes into the plasma state at the first high frequency current, the second gas ionizes into a plasma state at a second high frequency current, and the second high frequency current is higher than the first high frequency current.

In another aspect of the present disclosure, a method for controlling a flow of a first gas and a second gas, a first gas source configured to supply the first gas through the first gas channel, and a second gas source configured to supply the second gas through a second gas channel is disclosed. The method comprises supplying the first gas through the first gas channel aimed to reach beyond the distal end of an electrode, supplying a second gas through the second gas channel not aimed to reach beyond the distal end of an electrode, and applying a first high frequency current to the electrode to ionize the first gas to a plasma state, wherein the first high frequency current is sufficient to ionize the first gas into a plasma state. The supply of the second gas is stopped prior to stopping the supply of the first gas or stopping the application of the first high frequency current and the first gas ionizes into the plasma state at the first high frequency current, the second gas ionizes into a plasma state at a second high frequency current, and the second high frequency current is higher than the first high frequency current.

In another aspect of the present disclosure, a method of controlling a flow of a first gas and a second gas, a first gas source configured to supply the first gas through the first gas channel, and a second gas source configured to supply the second gas through a second gas channel is disclosed. The method comprises supplying the first gas through the first gas channel aimed to reach beyond the distal end of an electrode, supplying a second gas through the second gas channel not aimed to reach beyond the distal end of an electrode, and applying a first high frequency current to the electrode to ionize the first gas to a plasma state, wherein the first high frequency current is sufficient to ionize the first gas into a plasma state. The supply of the second gas is stopped prior to stopping the supply of the first gas or stopping the application of the first high frequency current and the first gas ionizes into the plasma state at the first high frequency current, the second gas ionizes into a plasma state at a second high frequency current, and the second high frequency current is higher than the first high frequency current.

In another aspect of the present disclosure, the second gas is supplied prior to or simultaneously with supplying the first gas or the second gas is supplied prior to or simultaneously with applying the first high frequency current. Furthermore, in some embodiments, the first gas ionizes into the plasma state at a first high frequency current, the second gas ionizes into a plasma state at a second high frequency current, and the second high frequency current is higher than the first high frequency current. In some embodiments, the first gas is an inert gas, such as Argon and second gas is carbon dioxide, and the first high frequency current is sufficient to only ionize the first gas, e.g., Argon, into the plasma state.

In another aspect of the present disclosure, the second gas is supplied after supplying the first gas and the applying the first high frequency current.

In another aspect of the present disclosure, the supply of the second gas is stopped prior to stopping the supply of the first gas or stopping the application of the first high frequency current.

In another aspect of the present disclosure, the second gas is supplied prior to supplying the first gas and the first gas is supplied prior to applying the first high frequency current.

In another aspect of the present disclosure, the second gas is supplied prior to applying the first high frequency current and the first high frequency current is applied prior to supplying the first gas.

In another aspect of the present disclosure, the second gas is supplied prior to supplying the first gas and applying the first high frequency current simultaneously.

In another aspect of the present disclosure, the first and second gas are supplied simultaneously and prior to applying the first high frequency current.

In another aspect of the present disclosure, the supply of second gas and application of the first high frequency current occurs simultaneously and prior to supplying the first gas.

In another aspect of the present disclosure, the supply of first and second gas and application of the first high frequency current occurs simultaneously.

In another aspect of the present disclosure, the first gas is supplied prior to supplying the second gas and the second gas is supplied prior to applying the first high frequency current.

In another aspect of the present disclosure, the first gas is supplied prior to applying the first high frequency current and supplying the second gas simultaneously.

In another aspect of the present disclosure, the first high frequency current is applied prior to supplying the second gas and the second gas is supplied prior to supplying the first gas.

In another aspect of the present disclosure, the first high frequency current is applied prior to supplying the first and second gas simultaneously.

In another aspect of the present disclosure, the supply of the second gas is stopped prior to stopping the supply of the first gas and the supply of the first gas is stopped prior to stopping the application of the first high frequency current.

In another aspect of the present disclosure, the supply of the second gas is stopped prior to stopping the supply of the first high frequency current and the application of the first high frequency current is stopped prior to stopping the supply of the first gas.

In another aspect of the present disclosure, the supply of the second gas is stopped prior to simultaneously stopping the supply of the first gas and the application of the first high frequency current.

In another aspect of the present disclosure, the supply of the first and second gas are simultaneously stopped prior to stopping the application of the first high frequency current.

In another aspect of the present disclosure, the supply of the second gas and application of the first high frequency are simultaneously stopped prior to stopping the supply of the first gas.

In another aspect of the present disclosure, the supply of the first and second gas and application of the first high frequency current are stopped simultaneously.

In another aspect of the present disclosure, the supply of the first gas is stopped prior to stopping the supply of the second gas and supply of the second gas is stopped prior to stopping the application of the first high frequency current.

In another aspect of the present disclosure, the supply of the first gas is stopped prior to stopping the application of the first high frequency current and application of the first high frequency is stopped prior to stopping the supply of the second gas.

In another aspect of the present disclosure, the supply of the first gas is stopped prior to simultaneously stopping the supply of the second gas and stopping the application of the first high frequency current.

In another aspect of the present disclosure, the supply of the first gas and application of the first high frequency current is simultaneously stopped prior to stopping the supply of the second gas.

In another aspect of the present disclosure, the application of the first high frequency current is stopped prior to stopping the supply of the second gas and the supply of the second gas is stopped prior to stopping the supply of the first gas.

In another aspect of the present disclosure, the application of the first high frequency current is stopped prior to stopping the supply of the first gas and supply of the first gas is stopped prior to stopping the supply of the second gas.

In another aspect of the present disclosure, the application of the first high frequency current is stopped prior to simultaneously stopping the supply of the first gas and second gas In another aspect of the present disclosure, the supply of the second gas is stopped after stopping the supply of the first gas or after stopping the application of the first high frequency current.

The term "patient," as used herein, comprises any and all organisms and includes the term "subject." A patient can be a human or an animal.

Other systems, methods, features and advantages will be, or will become, apparent to one with skill in the art upon examination of the following figures and detailed description. It is intended that all such additional systems, methods, features and advantages be included within this description, be within the scope of the present disclosure, and be protected by the following claims. Nothing in this section should be taken as a limitation on those claims. Further aspects and advantages are discussed below in conjunction with the embodiments of the disclosed input device. It is to be understood that both the foregoing general description and the following detailed description of the disclosed input device are examples and explanatory and are intended to provide further explanation of the disclosed input device as claimed.

BRIEF DESCRIPTION OF THE DRAWING

The following detailed description of preferred embodiments can be read in connection with the accompanying drawings in which like numerals designate like elements and in which:

FIGS. 6A to 6D illustrates the frontal view of the ablation treatment devices appearing from the channel opening of the endoscope device.

FIG. 8 is a chart listing various control sequences for commencing the ablation treatment procedure.

FIG. 9 is a chart listing various control sequences for halting the ablation treatment procedure.

FIG. 10 is a chart listing other various control sequences for commencing the ablation treatment procedure.

FIG. 11 is a chart listing further various control sequences for commencing the ablation treatment procedure.

FIG. 12 is a chart listing other various control sequences for halting the ablation treatment procedure.

FIG. 13 is a chart listing further various control sequences for halting the ablation treatment procedure.

Figure 1:
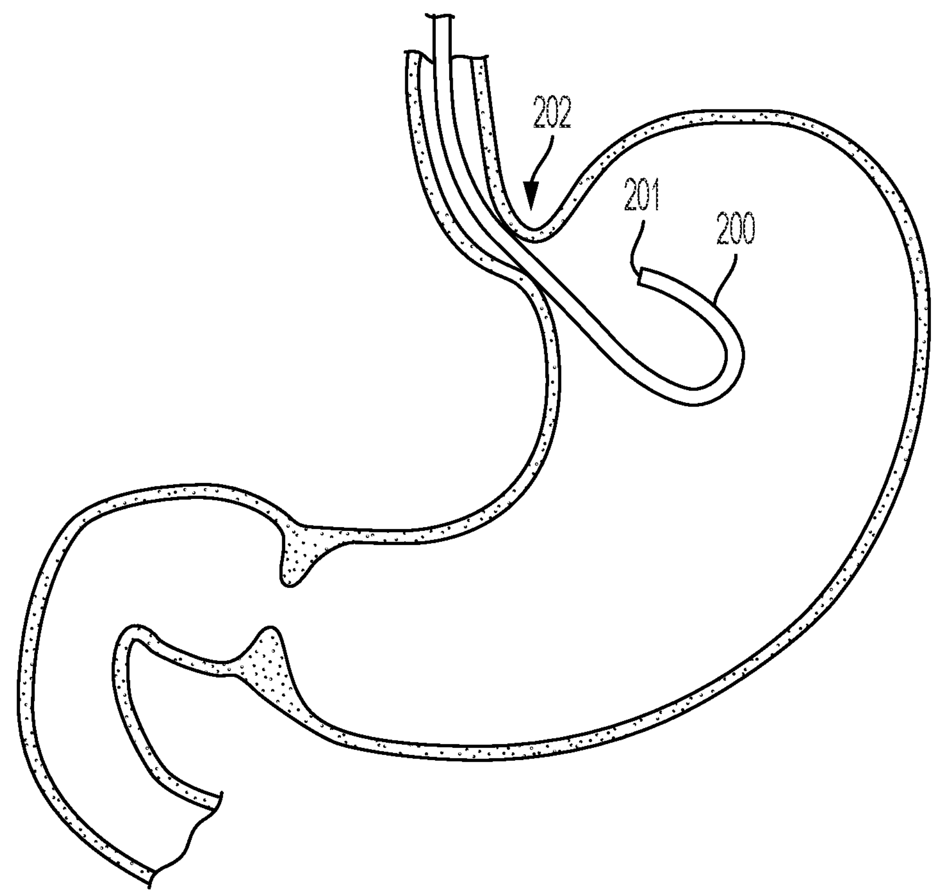
FIG. 1 illustrates a sectional view of the human stomach with an endoscope device inserted for performing the ablation procedure.

Throughout all of the drawings, dimensions of respective constituent elements are appropriately adjusted for clarity. For ease of viewing, in some instances only some of the named features in the figures are labeled with reference numerals.

DETAILED DESCRIPTION

FIG. 1 is an illustration of a sectional view of the human stomach with an endoscope device 200 inserted for performing the ablation treatment procedure. The distal tip 201 of the endoscope device 200 is pointed towards the gastroesophageal junction 202 for observing the site of the operation prior to performing the ablation procedure.

Figure 2:
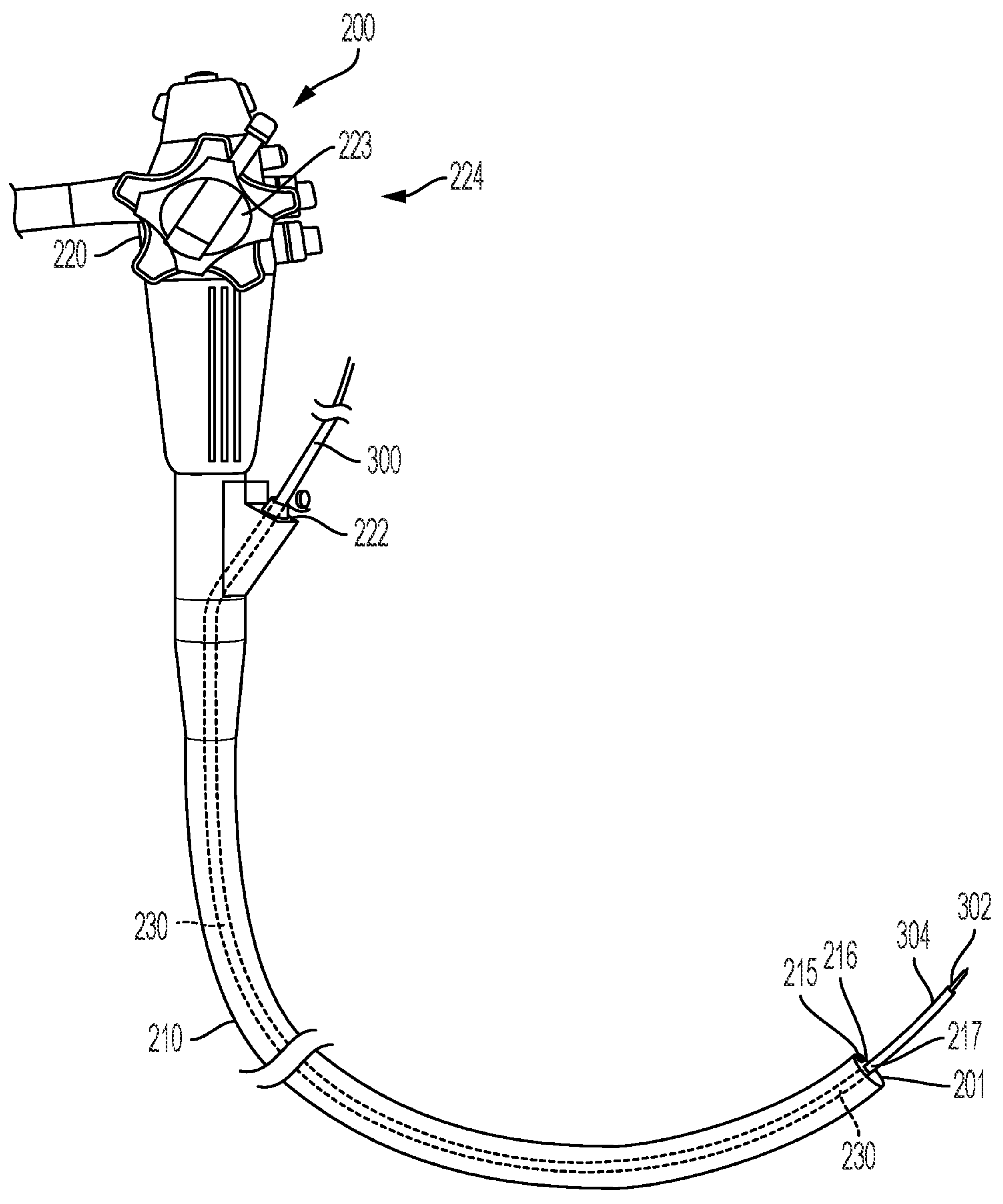
FIG. 2 illustrates the endoscope device having an ablation treatment device inserted within a treatment device channel.

FIG. 2 is an illustration of the endoscope device 200. The endoscope device 200 includes a distal tip 201, an insertion tube 210, and an operating portion 220. The distal tip 201 includes a camera portion 215 and a lighting portion 216 used for observing inner objects of the human body. The insertion tube 210 includes a treatment device channel 230 extending from the insertion opening 222 to the distal tip 201. The ablation treatment device and optionally other surgical treatment devices can be inserted into the treatment device channel 230, extend the length of the insertion tube, and then end at or protrude from channel opening 217 at the distal tip 201 of the endoscope device 200 For example, in FIG. 2, the electrode 302 and the treatment tube 304 are shown protruding from the channel opening 217 at the distal tip 201.

Figure 3:
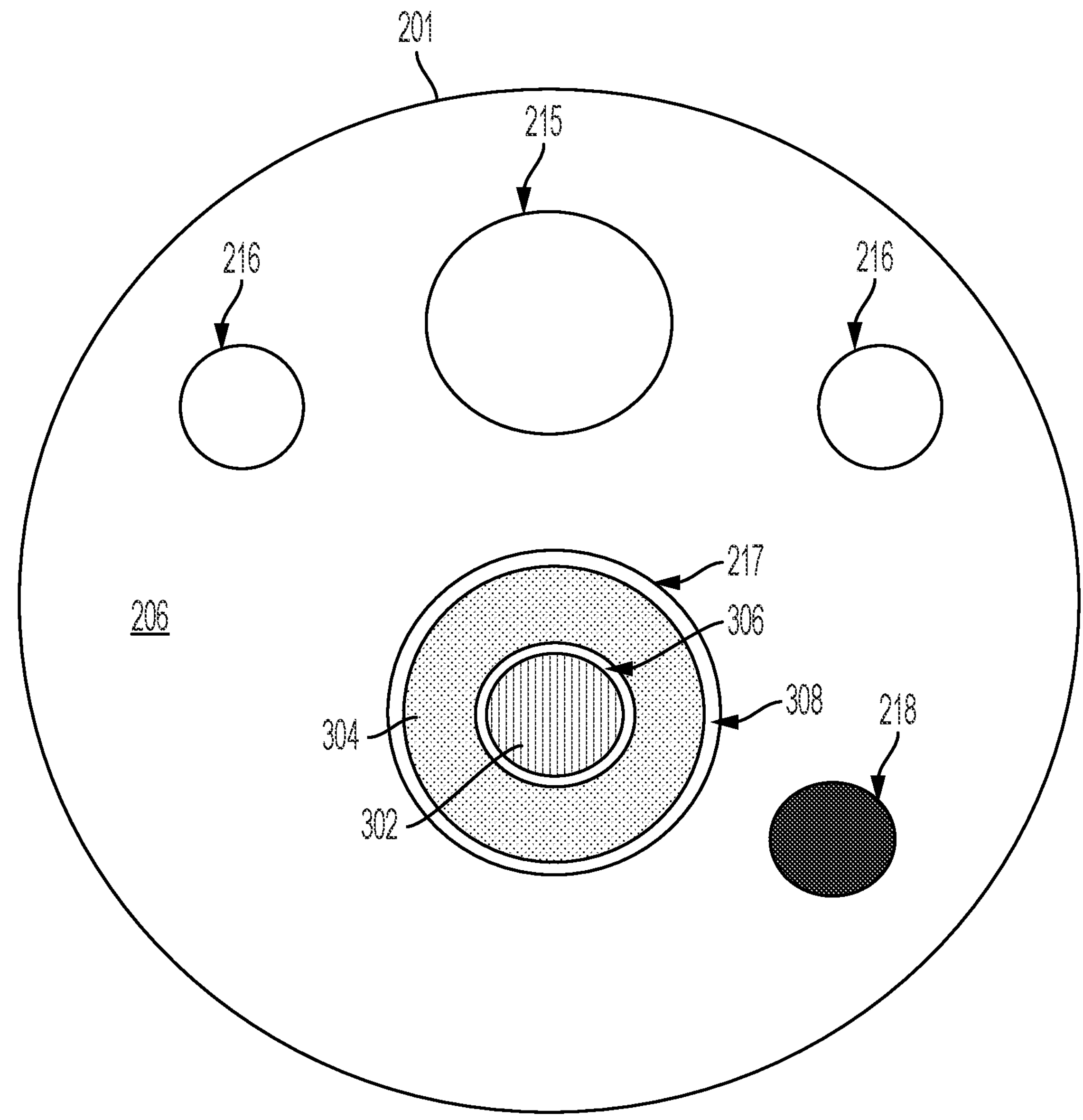
FIG. 3 illustrates the frontal view of the distal tip of the endoscope device and showing the tip of the ablation treatment device in the channel opening of the endoscope device.

FIG. 3 is an illustration of the face surface 206 of the distal tip 201 of the endoscope device 200. The camera portion 215 and the two lighting portions 216 are used for observing the site of operation. Within channel opening 217 are the electrode 302 and the treatment tube 304 of the ablation treatment device 300. The electrode 302 and the treatment tube 304 are slidably disposed in the treatment device channel 230 and can be manipulated independently to, for example, each protrude from the channel opening 217 and past a plane containing the face surface 206 of the distal tip 201. Because of the electrode 302 within the treatment tube 304 within the treatment device channel 230, there are gaps between these various features and each of these gaps form a passage for the passage of, for example, gases and fluids. Thus, for example, an inner tube channel 306 is formed between an outer surface of the electrode 302 and an inner surface of treatment tube 304 and this inner tube channel 306 allows gas and/or liquid to be injected to and retrieved from the site of operation. Also, for example, an outer tube channel 308 is formed between an outer surface of the treatment tube 304 and the inner surface of the channel opening 217 and this outer tube channel 308 also allows gas and/or liquid to be injected to and retrieved from the site of operation. In addition, a multipurpose channel 218 of the endoscope device 200 opens in the face surface 206 of the distal tip 201 and also allow gas and/or liquid to be injected to and retrieved from the site of operation. The multipurpose channel 218 may be formed in various locations of the face surface 206 of distal tip 201 and can have various sizes and be present in various numbers.

Figure 4A:
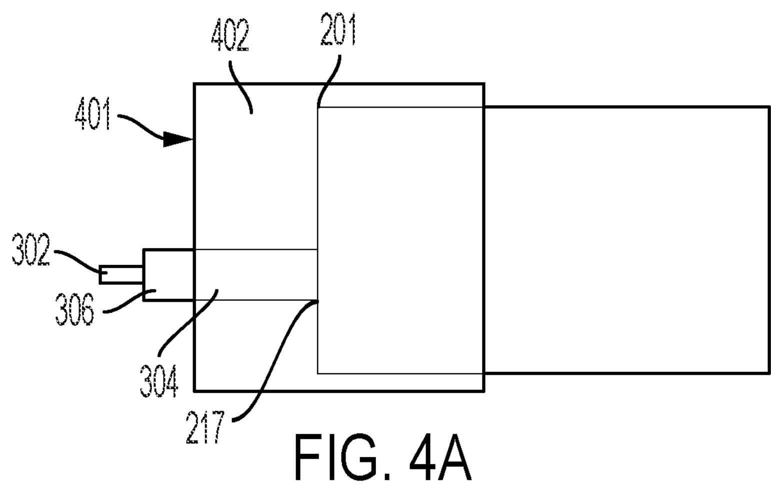
FIGS. 4A to 4C are side views schematically illustrating the distal tip of the endoscope device during the ablation procedure.

FIG. 4A schematically illustrates, in magnified side view, the distal tip 201 of the endoscope device 200 in a condition in which the ablation treatment device 300 is ready to be used. A cap 402 is attached to the distal tip 201 in order to improve visibility of the operating site through the camera portion 215 during the operation. The cap 402 may be made from transparent resin or glass material. Ablation treatment device 300 protrudes out from the channel opening 217, sufficient to position the electrode 302 and inner tube channel 306 past a face 401 of and outside the cap 402.

Figure 4B:
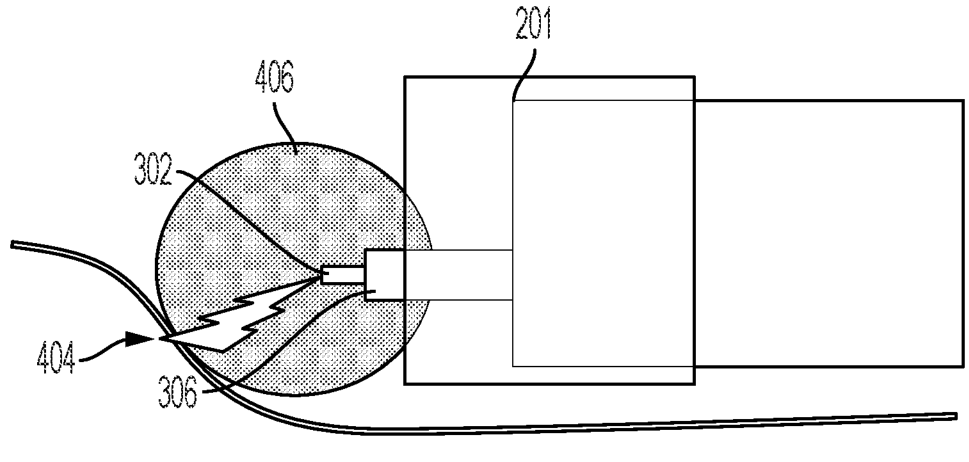

FIG. 4B schematically illustrates, in magnified side view, the distal tip 201 of the endoscope device 200 in a condition in which the ablation treatment device 300 is in the process of conducting the ablation procedure. An inert gas, preferably Argon, is injected in the direction of the ablation target area 404 from the inner tube opening 306. The reason Argon is preferred as an inert gas is due to its capability to be ionized into a plasma state at a relatively low voltage compared to other inert gases. To prevent unintended discharge and ablation to occur, the level of voltage applied to the electrode 302 is adjusted to ensure that only Argon, and no other inert gas or naturally existing gases, would be converted into a plasma state and create a discharge. Through the injection of the inert gas, an inert gas atmosphere 406 will be formed near the ablation target area 404. This inert gas atmosphere 406 is the medium through which the electrode 302 applies high frequency (HF) currents to the ablation target area 404. As the result of the HF current coming in contact with the inert gas atmosphere 406, inert gas (Argon) is ionized into a plasma state, causing discharging to occur. Because the electrode 302 is a neutral electrode, the discharge would occur between the electrode 302 and a target in the vicinity, which in this case is the ablation target area 404. The optimal operative distance from the protruding distal tip of the electrode 302 to the distal tip 201 of the endoscope device 200 is between 8 to 18 mm. In case the distance becomes larger than 18 mm, the distance between the ablation target area 404 and the camera portion 215 would be too far away negatively affecting the visibility of the medical operators performing the medical procedure. The electrode 302 and treatment tube 304 protruding too much from the distal tip 201 may also block the view of the medical operators checking on the ablation progress by blocking the scope of the camera portion 215. In case the distance between the protruding distal tip of the electrode 302 and the distal tip 201 of the endoscope device 200 becomes smaller than 8 mm, which roughly equals the distance from the distal tip of the cap 402 to the distal tip 201, the risk of inert gas accumulating within the cap 402 risking undesired discharging increases.

Figure 4C:
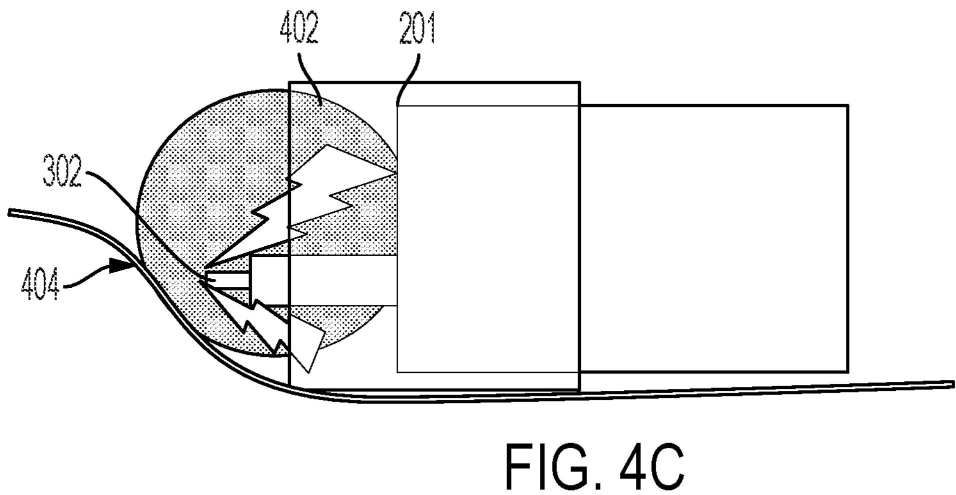

FIG. 4C schematically illustrates, in magnified side view, the distal tip 201 of the endoscope device 200 in a condition in which the ablation treatment device 300 is in the process of conducting the ablation procedure. In FIG. 4C, the distal tip of the electrode 302 protrudes about 8 to 18 mm from the distal tip 201. When the inert gas, preferably Argon, is injected in the vicinity of the ablation target area 404 from the inner tube opening 306, the inert gas would accumulate within the cap 402, causing the insert gas atmosphere 406 to accumulate within cap 402 and contact the distal tip 201 of the endoscope device 200. In this case, the discharge can occur within the insert gas atmosphere 406 between the electrode 302 and the cap 402 or between the electrode 302 and the distal tip 201, damaging the cap 402 and/or electronics devices placed at the distal tip 201, such as camera portion 215 or lighting portion 216. The damaging of the cap 402 or the distal tip 201 through the discharge not only damages the endoscope, but causes health concerns for the patient and, therefore, should be avoided.

Figure 5A:
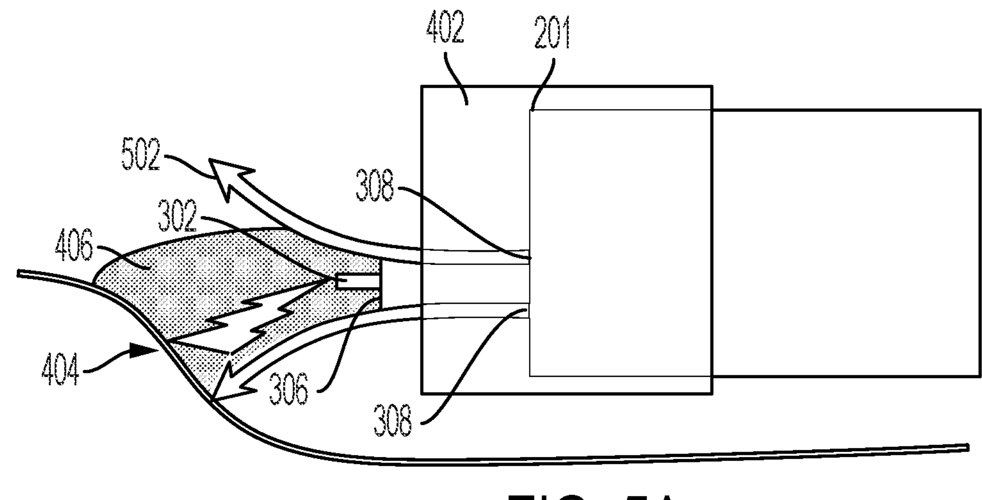
FIGS. 5A to 5C are side views schematically illustrating the distal tip of the endoscope device during the ablation procedure with injection of the $CO_2$ gas.

FIG. 5A schematically illustrates, in magnified side view, the distal tip 201 of the endoscope device 200 in a condition in which the ablation treatment device 300 is used for the ablation procedure. A first gas, such as an inert gas, preferably Argon, is injected in the vicinity of the ablation target area 404 from the inner tube opening 306. A second gas that ionizes into the plasma state at a high frequency current that is higher than that for ionizing the first gas into the plasma state is injected through the outer tube channel 308 forming gas flow 502. A suitable first gas is Argon and a suitable second gas that ionizes into the plasma state at a high frequency current that is higher than that for ionizing Argon is, for example $CO_2$ gas and the example embodiments will be discussed in the context of these two gases. Gas flow 502 pushes the inert gas atmosphere 406 from the Argon gas out from the cap 402 and towards the ablation target area 404. The second gas flow 502 from the $CO_2$ gas enables the inert gas atmosphere 406 from the Argon gas to accumulate near the ablation target area 404 with more efficiency compared to the case in FIG. 4B. In other words, the inert gas atmosphere 406 from the Argon gas is concentrated in the vicinity of ablation target area 404 and is displaced from or forced away from non-ablation areas, such as the interior volume of the cap 402 and the region in front of the face surface 206 of the distal tip 201, by the second gas flow 502 from the $CO_2$ gas. After the inert gas atmosphere 406 from the Argon gas is formed in the vicinity of the ablation target area 404, the HF current applied through electrode 302 causes discharges to occur within the inert gas atmosphere 406 from the Argon gas, ablating the ablation target area 404.

Figure 5B:
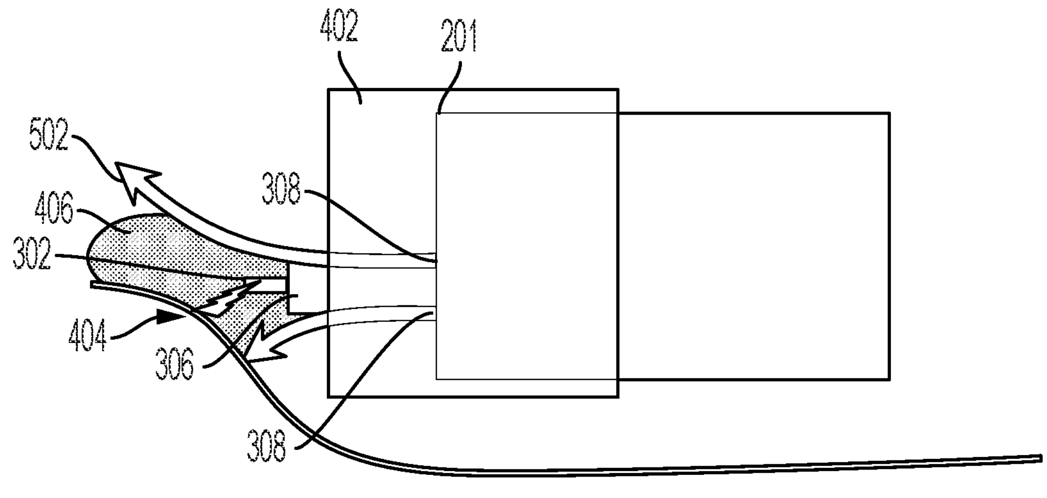

FIG. 5B schematically illustrates, in magnified side view, the distal tip 201 of the endoscope device 200 in a condition in which the ablation treatment device 300 is used for the ablation procedure. In FIG. 5B, the electrode 302 distal tip of the electrode 302 protrudes about 8 to 18 mm from the distal tip 201. When the inert gas, preferably Argon, is injected in the direction of the ablation target area 404 from the inner tube opening 306, a second gas, preferably $CO_2$ gas, is injected through the outer tube channel 308 forming gas flow 502. The gas flow 502 from the $CO_2$ gas pushes the inert gas atmosphere 406 from the Argon gas out from the cap 402 and towards the ablation target area 404, preventing the inert gas from accumulating within the cap 402. The gas flow 502 from the $CO_2$ gas also prevents the insert gas atmosphere 406 from the Argon gas from contacting the distal tip 201 of the endoscope device 200, preventing any discharges to occur between the electrode 302 and the cap 402 or distal tip 201.

Figure 5C:
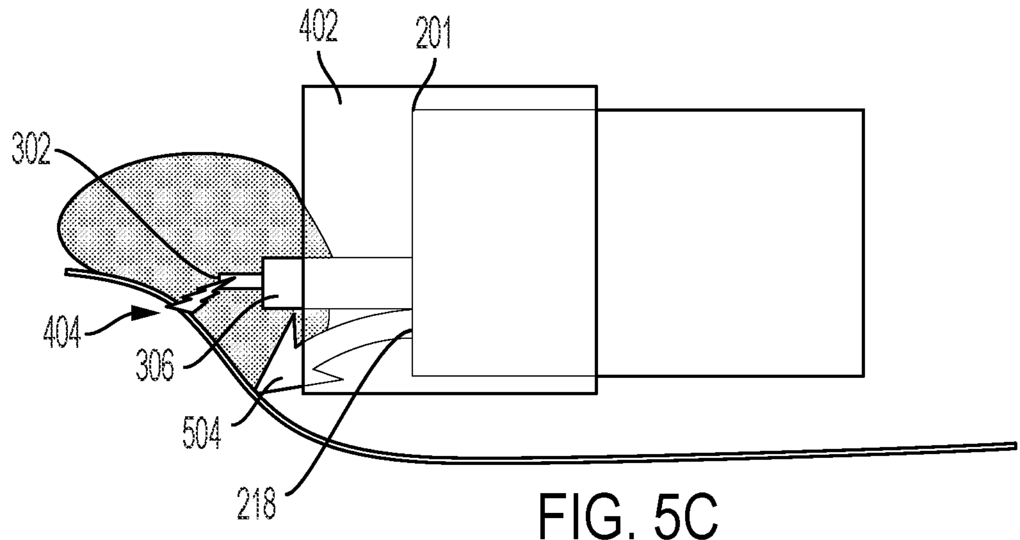

FIG. 5C schematically illustrates, in magnified side view, the distal tip 201 of the endoscope device 200 in a condition in which the ablation treatment device 300 is used for the ablation procedure. In FIG. 5C, the electrode 302 distal tip of the electrode 302 protrudes about 8 to 18 mm from the distal tip 201. When the inert gas, preferably Argon, is injected in the direction of the ablation target area 404 from the inner tube opening 306, a second gas preferably $CO_2$ gas, is injected through the multipurpose channel 218 forming gas flow 504. The gas flow 504 injected from the multipurpose channel 218 may be stronger than the gas flow injected from outer tube channel 308. The gas flow 504 of $CO_2$ gas from the multipurpose channel 218 pushes the inert gas atmosphere 406 from the Argon gas out from the cap 402 and towards the ablation target area 404, preventing the inert gas from accumulating within the cap 402. The gas flow 504 of $CO_2$ gas from the multipurpose channel 218 also prevents the insert gas atmosphere 406 from the Argon gas from contacting the distal tip 201 of the endoscope device 200, preventing any discharges to occur between the electrode 302 and the cap 402 or distal tip 201. The gas flow 504 injected from the multipurpose channel 218 may be used independently or in combination with gas flow 502 from the $CO_2$ gas injected from outer channel 308.

Generally speaking, by making the flow rate of $CO_2$ gas faster than that of inert gas, it is possible to suppress the discharge between the electrode 302 and the cap 402 or distal tip 201. On the other hand, by making the flow rate of the inert gas faster than that of the $CO_2$ gas, it is possible to discharge stably into the ablation target area 404 without being affected by the $CO_2$ gas.

FIGS. 6A to 6D are illustration of various shapes of the exterior surface of treatment tube 304 of the ablation treatment device 300 allowing an increased volume and/or the formation of discrete channels for gas and/or liquid to flow through the outer tube channel 308. In FIG. 6A, the exterior surface of the treatment tube 304 has triangular-shaped recesses 602. In FIG. 6B, the exterior surface of the treatment tube 304 has curve-shaped recesses 604. In FIG. 6C, the exterior surface of the treatment tube 304 has flattened structures 606 forming flat surfaces. In FIG. 6D, the exterior surface of the treatment tube 304 has block-shaped recesses 608. The various structures/recesses in each of the embodiments can be distributed symmetrically about the axis of the treatment tube 304. For example, three-fold, four-fold, five-fold and six-fold symmetry can be used.

Figure 7:
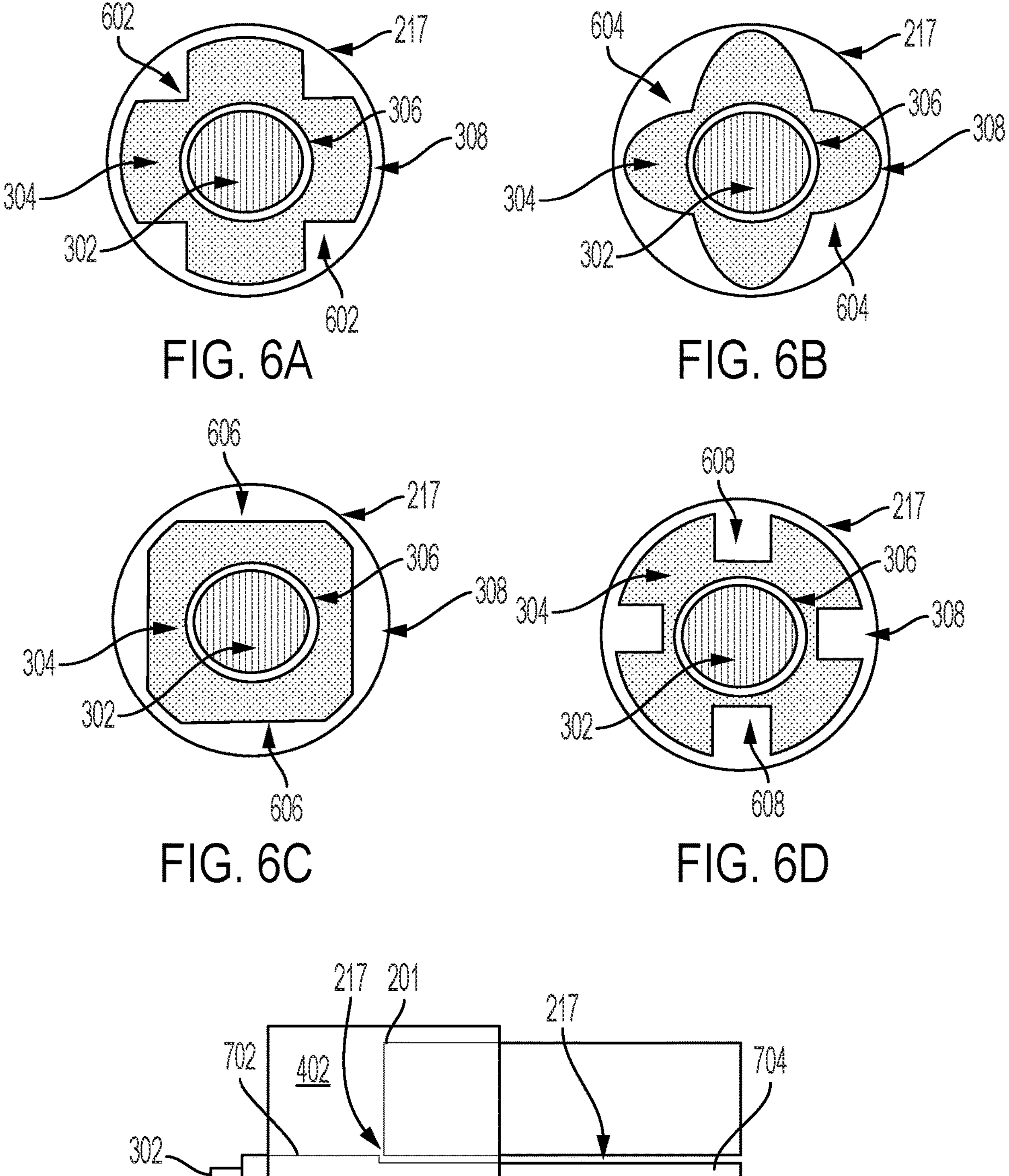
FIG. 7 illustrate the side view of the distal tip of the endoscope device.

FIG. 7 schematically illustrates a cross-sectional side view of the distal tip 201 of the endoscope device 200 and the ablation treatment device 300. The treatment tube 304 of the ablation treatment device 300 has two portions each having different diameters—outer tube portion 702 and inner tube portion 704. The outer diameter of the outer tube portion 702 is the same or slightly smaller than the inner diameter of channel opening 217. Through this configuration, the operator would be able to sense the contacting of the outer tube portion 702 with the rim of the channel opening 217 or the friction made between outer tube portion 702 and the treatment device channel 230, and use the received sensation as an indicator to determine the location of the outer tube portion 702 in relation to the channel opening 217. The distance 706 of the outer tube portion 702 is preferably set at more than 10 mm, enough distance to allow the treatment tube 304 and electrode 302 to stick out from cap 402 when the outer tube portion 702 and the rim of the channel opening 217 makes contact. This configuration allows the operator to set the ablation treatment device 300 at an optimal location in relation to the endoscope device 200 and the attached cap 402. By preventing the electrode 302 and inner tube channel 306 to be located within the cap 402, the configuration prevents the inert gas atmosphere 406 from the Argon gas to be accumulated within the cap 402, thereby reducing the risk of discharge occurring between the electrode 302 and the cap 402 or distal end 201.

By making the flow rate of $CO_2$ gas faster than that of inert gas, it is possible to suppress the discharge between the electrode 302 and the cap 402 or distal tip 201.

On the other hand, by making the flow rate of the inert gas faster than that of the $CO_2$ gas, it is possible to discharge stably into the ablation target area 404 without being affected by the $CO_2$ gas.

FIGS. 8 to 13 are charts describing different patterns of administrative control sequences for controlling the endoscope device 200 and ablation treatment device 300 for commencing the ablation treatment procedure. Since both hands of the medical operator are occupied during the ablation treatment procedure, the medical operator will likely use a foot switch for turning on and off of the activities related to the ablation treatment procedure. Each time the foot switch is operated, the controlling device instructs the endoscope device 200 or the ablation treatment device 300 to perform the steps described in FIGS. 8-13, namely the 1st step, the 2nd step, and the 3rd step. The transition to the next step does not mean the previous activity is halted. Rather, the activities of the previous steps continue unless such activity is turned off during one of the steps further described in connection with the control sequences for halting the ablation treatment procedure disclosed herein, for example, in FIGS. 9, 12 and 13.

In the control sequence for commencing the ablation treatment procedure in FIGS. 8, 10 and 11, the term "Insert Gas" represents the instruction to inject the inert first gas (preferably Argon gas) from inner tube channel 304. Similarly, the term "$CO_2$" represents the instruction to inject the second gas, i.e., the gas that ionizes into the plasma state at a high frequency current that is higher than that for ionizing the first gas into the plasma state (preferably $CO_2$ gas) from the outer tube channel 308 or the multipurpose channel 218. Finally, the term "HF" represents the instruction to apply the high-frequency (HF) current from electrode 302 to cause discharges and ablation. In case any two or more of the instruction terms ($CO_2$, Inert Gas, and HF) are described within a single step, it means that the multiple instructions are operated simultaneously.

In the control sequence for halting the ablation treatment procedure in FIGS. 9, 12 and 13, the term "Insert Gas"

represents the instruction to halt injecting the inert first gas (preferably Argon gas) from inner tube channel 304. Similarly, the term "$CO_2$" represents the instruction to halt inject the second gas, i.e., the gas that ionizes into the plasma state at a high frequency current that is higher than that for ionizing the first gas into the plasma state (preferably $CO_2$ gas) from the outer tube channel 308 or the multipurpose channel 218. Finally, the term "HF" represents the instruction to halt application of the high-frequency (HF) current from electrode 302 to stop discharges and ablation. In case any two or more of the instruction terms ($CO_2$, Inert Gas, and HF) are described within a single step, it means that the multiple instructions are operated simultaneously.

FIG. 8 is a chart describing different patterns of administrative control sequences (labeled as Seq. No. in FIG. 8) for controlling the endoscope device 200 and ablation treatment device 300 for commencing the ablation treatment procedure.

In sequence no. 1, the $CO_2$ gas is injected during the 1st step, then the inert gas is injected during the 2nd step, and finally the HF current is applied during the 3rd step. During the 1st step, any remaining inert gas from previous procedures are pushed out from cap 402 and away from distal tip 201 by the injected $CO_2$ gas. The insert gas injected during the 2nd step accumulates near the ablation target area 404, while continuously injected $CO_2$ gas prevents the inert gas from accumulating inside or near cap 402 or distal tip 201. The HF current applied during the 3rd step will cause discharges to occur within the inert gas atmosphere 406 and ablate the ablation target area 404 without the concern of discharge occurring between electrode 302 and cap 402 or distal tip 201.

In sequence no. 2, $CO_2$ gas is injected during the 1st step, then the HF current is applied during the 2nd step, and finally the inert gas is injected during the 3rd step. During the 1st step, any remaining inert gas from the previous procedures are pushed out from the cap 402 or distal tip 201 by the injected $CO_2$ gas. The HF current applied during the 2nd step will not create any discharge due to HF current being insufficient to ionize the injected $CO_2$ gas, but the HF current would be sufficient to create discharge between the electrode 302 and the ablation target area 404 after the insert gas atmosphere 406 is formed in the 3rd step, while continuously injected $CO_2$ gas prevents the inert gas from accumulating inside or near cap 402 or distal tip 201.

In sequence no. 3, $CO_2$ gas is first injected during the 1st step, then the application of the HF current and injection of the inert gas occurs simultaneously during the 2nd step (no 3rd step for seq. no. 3). During the 1st step, any remaining inert gas from the previous procedures are pushed out from the cap 402 or distal tip 201 by the injected $CO_2$ gas. The HF current applied and inert gas injected during the 2nd step will create discharges between the electrode 302 and the ablation target area 404 after the insert gas atmosphere 406 is formed, while continuously injected $CO_2$ gas prevents the inert gas from accumulating inside or near cap 402 or distal tip 201.

In sequence no. 4, $CO_2$ gas and insert gas are simultaneously injected during the 1st step, then the application of the HF current occurs during the 2nd step (no 3rd step for seq. no. 4). During the 1st step, any remaining inert gas from the previous procedures are pushed out from the cap 402 or distal tip 201 by the injected $CO_2$ gas, and inert gas atmosphere 406 is formed near the ablation target area 404. The HF current applied during the 2nd step will create discharges between the electrode 302 and the ablation target area 404, while continuously injected $CO_2$ gas prevents the inert gas from accumulating inside or near cap 402 or distal tip 201.

In sequence no. 5, injection of $CO_2$ gas and application of HF current occurs simultaneously during the 1st step, then the injection of the insert gas occurs during the 2nd step (no 3rd step for seq. no. 5). During the 1st step, any remaining inert gas from the previous procedures are pushed out from the cap 402 or distal tip 201 by the injected $CO_2$ gas, and application of the HF current does not create any discharges due to the $CO_2$ gas. The discharge between the electrode 302 and the ablation target area 404 will occur only after the insert gas atmosphere 406 is formed near the ablation target area 404 during the 2nd step, while continuously injected $CO_2$ gas prevents the inert gas from accumulating inside or near cap 402 or distal tip 201.

In sequence no. 6, injection of $CO_2$ gas and insert gas, as well as the application of HF current occurs simultaneously during the 1st step (no 2nd or 3rd step for seq. no. 6). During the 1st step, any remaining inert gas from the previous procedures are pushed out from the cap 402 or distal tip 201 by the injected $CO_2$ gas, while insert gas atmosphere 406 is formed near the ablation target area 404. The application of the HF current will create discharges between electrode 302 and the ablation target area 404 as soon as the insert gas atmosphere 406 is formed near the ablation target area 404, while continuously injected $CO_2$ gas prevents the inert gas from accumulating inside or near cap 402 or distal tip 201.

In sequence no. 7, the inert gas is first injected towards the ablation target area 404 during the 1st step, then $CO_2$ gas is injected from the during the 2nd step, and then finally the HF current is applied during the 3rd step. During the 1st step, the injected insert gas forms the insert gas atmosphere 406 in the vicinity of the inner tube channel 304. The $CO_2$ gas injected during the 2nd step pushes out the accumulated inert gas and other dischargeable gas out from cap 402 and away from distal tip 201, while forming the inert gas atmosphere in the vicinity of the ablation target area 406. The HF current applied during the 3rd step will discharge and ablate the ablation target area 404 without the concern of discharge occurring between the electrode 302 and the cap 402 or distal tip 201.

In sequence no. 8, the inert gas is injected during the 1st step, the HF current is applied during the 2nd step, and then the $CO_2$ gas is injected during the 3rd step. During the 1st step, the injected insert gas forms the insert gas atmosphere 406 near the inner tube channel 304. The HF current applied during the 2nd step will create a discharge between the electrode 302 and ablation target area 404. The $CO_2$ gas injected during the 3rd step will prevent discharges from occurring between the electrode 302 and the cap 402 or distal tip 201.

In sequence no. 9, the inert gas is injected during the 1st step, then the application of the HF current and injection of the $CO_2$ gas occurs simultaneously during the 2nd step (no 3rd step for seq. no. 9). During the 1st step, the injected insert gas will form the insert gas atmosphere 406 near the inner tube channel 304. The HF current applied during the 2nd step will create a discharge between the electrode 302 and ablation target area 404, while the simultaneously injected $CO_2$ gas will prevent discharges from occurring between the electrode 302 and the cap 402 or distal tip 201.

In sequence no. 10, the injection of the inert gas and application of the HF current occurs simultaneously during the 1st step, then the injection of the $CO_2$ gas occurs during the 2nd step (no 3rd step for seq. no. 10). During the 1st step, the injected insert gas will form the insert gas atmosphere 406 near the inner tube channel 304 and the simultaneously applied HF current will create a discharge between the electrode 302 and ablation target area 404. The $CO_2$ gas injected during the 2nd step will prevent discharges from occurring between the electrode 302 and the cap 402 or distal tip 201.

In sequence no. 11, the HF current is applied during the 1st step, the injection of the $CO_2$ gas occurs during the 2nd step, and the injection of the inert gas occurs during the 3rd step. During the 1st step, the applied HF current will not create discharges due to lack of insert gas atmosphere 406. During the 2nd step, the injected $CO_2$ gas pushes out and replaces any gas remaining in cap 402. Discharges may occur after the insert gas atmosphere 406 is created between the electrode 302 and ablation target area 404 during the 3rd step.

In sequence no. 12, the HF current is applied during the 1st step, the injection of the inert gas occurs during the 2nd step, and the injection of the $CO_2$ gas occurs during the 3rd step. During the 1st step, the applied HF current will not create discharges due to lack of insert gas atmosphere 406. During the 2nd step, discharges may occur after the insert gas atmosphere 406 is created between the electrode 302 and ablation target area 404. The injected $CO_2$ gas pushes out any gas remaining in cap 402 other than the inert gas continuously injected through inner tube channel 306.

In sequence no. 13, the HF current is applied during the 1st step, and the injection of the inert gas and $CO_2$ gas occurs during the 2nd step (no 3rd step for seq. no. 13). During the 1st step, the applied HF current does not create discharges due to lack of insert gas atmosphere 406. During the 2nd step, discharges will occur after the insert gas atmosphere 406 is created between the electrode 302 and ablation target area 404, while the simultaneously injected $CO_2$ gas pushes out any gas remaining in cap 402 to prevent unintended discharges.

FIG. 9 is a chart describing different patterns of administrative control sequences (labeled as Seq. No. in FIG. 9) for controlling the endoscope device 200 and ablation treatment device 300 for halting the ablation treatment procedure. Specifics of the sequences 14 to 26 are described below using the same terminology and operation methods used in FIG. 8.

In sequence no. 14, the injection of $CO_2$ gas is stopped during the 1st step, then the injection of the inert gas is stopped during the 2nd step, and then the application of the HF current is stopped during the 3rd step. The discharge and the ablation procedure continue after the $CO_2$ gas is no longer injected during the 1st step, but may halt during the 2nd step when the inert gas is no longer injected and the insert gas atmosphere 406 is consumed or dissipates and no longer supports ionization. Even if the discharge and the ablation procedure continue through the 2nd step, it will halt during the 3rd step when the application of the HF current is turned off.

In sequence no. 15, the injection of $CO_2$ gas is stopped during the 1st step, then the application of the HF current is stopped during the 2nd step, and then the injection of the inert gas is stopped during the 3rd step. The discharge and the ablation procedure continue after the $CO_2$ gas is no longer injected during the 1st step, but will halt during the 2nd step when the application of the HF current is turned off.

In sequence no. 16, the injection of $CO_2$ gas is stopped during the 1st step, then the application of the HF current and injection of the inert gas are stopped during the 2nd step (no 3rd step in seq. no. 16). The discharge and the ablation procedure continue after the $CO_2$ gas is no longer injected during the 1st step, but will halt during the 2nd step when the application of the HF current and the injection of the inert gas is turned off.

In sequence no. 17, the injection of $CO_2$ gas and inert gas are stopped during the 1st step, then the application of the HF current is stopped during the 2nd step (no 3rd step in seq. no. 17). The discharge and the ablation procedure may halt after the $CO_2$ gas and inert gas are no longer injected as the insert gas atmosphere 406 is consumed or dissipates and no longer supports ionization. The discharge and the ablation procedure will halt during the 2nd step when the application of the HF current is turned off.

In sequence no. 18, the injection of $CO_2$ gas and the application of the HF current are stopped during the 1st step, then the injection of the inert gas is stopped during the 2nd step (no 3rd step in seq. no. 18). The discharge and the ablation procedure will halt during the 1st step when the application of the HF current is turned off.

In sequence no. 19, the injection of $CO_2$ gas and inert gas, as well as the application of the HF current are all stopped during the 1st step (no 2nd or 3rd step in seq. no. 18). The discharge and the ablation procedure will halt after all three activities are turned off.

In sequence no. 20, the injection of the inert gas is stopped during the 1st step, then the injection of the $CO_2$ gas is stopped during the 2nd step, and then the application of the HF current is stopped during the 3rd step. The discharge and the ablation procedure will halt during the 1st step when the injection of the inert gas is stopped, since the insert gas atmosphere 406 between electrode 302 and ablation target area 404 will be pushed out by the continued injection of the $CO_2$ gas.

In sequence no. 21, the injection of the inert gas is stopped during the 1st step, then the application of the HF current is stopped during the 2nd step, and then the injection of the $CO_2$ gas is stopped during the 3rd step. The discharge and the ablation procedure will halt during the 1st step when the injection of the inert gas is stopped, since the insert gas atmosphere 406 between electrode 302 and ablation target area 404 will be pushed out by the continued injection of the $CO_2$ gas.

In sequence no. 22, the injection of the inert gas is stopped during the 1st step, then the application of the HF current and the injection of the $CO_2$ gas are stopped during the 2nd step (no 3rd step in seq. no. 22). The discharge and the ablation procedure will halt during the 1st step when the injection of the inert gas is stopped, since the insert gas atmosphere 406 between electrode 302 and ablation target area 404 will be pushed out by the continued injection of the $CO_2$ gas.

In sequence no. 23, the injection of the inert gas and application of the HF current is stopped during the 1st step, then the injection of the $CO_2$ gas is stopped during the 2nd step (no 3rd step in seq. no. 23). The discharge and the ablation procedure will halt during the 1st step after the injection of the inert gas and the application of the HF current are stopped.

In sequence no. 24, the application of the HF current is stopped during the 1st step, then the injection of the $CO_2$ gas is stopped during the 2nd step, and the injection of the inert gas is stopped during the 3rd step. The discharge and the ablation procedure will halt during the 1st step after the application of the HF current is stopped.

In sequence no. 25, the application of the HF current is stopped during the 1st step, then the injection of the inert gas is stopped during the 2nd step, and the injection of the $CO_2$ gas is stopped during the 3rd step. The discharge and the ablation procedure will halt during the 1st step after the application of the HF current is stopped.

In sequence no. 26, the application of the HF current is stopped during the 1st step, then the injection of the inert gas and $CO_2$ gas are stopped during the 2nd step (no 3rd step in seq. no. 26). The discharge and the ablation procedure will halt during the 1st step after the application of the HF current is stopped.

In sequence no. 1, 2, 3, 4, 5, 6, 7, 9, 11, and 13, the control circuit is programmed to supply the second gas prior to or simultaneously with supplying the first gas or supply the second gas prior to or simultaneously with applying the first high frequency current (Variation 1). The common advantage for the Variation 1 is that the injection of the $CO_2$ gas occurs prior to or simultaneously with the HF current applied to the inert gas thereby causing a discharge. The injected $CO_2$ gas serves to prevent unintended discharges occurring within the cap 402 and/or near the distal tip 201 of the endoscope device 200.

In sequence no. 8, 10, and 12, the control circuit is programmed to supply the second gas after supplying the first gas and the applying the first high frequency current (Variation 2). The common advantage for the Variation 2 is that the discharge may occur without waiting for the injection of the $CO_2$ gas, allowing immediate commencement of the treatment procedure that may also lead to shortening the time of the entire treatment procedure.

In sequence no. 14, 15, and 16, the control circuit is programmed to stop the supply of the second gas prior to stopping the supply of the first gas or stopping the application of the first high frequency current (Variation 3).

In sequence no. 17 to 26, the control circuit is programmed to stop the supply of the second gas after stopping the supply of the first gas or stopping the application of the first high frequency current (Variation 4). The common advantage for the Variation 4 is that the injection of the $CO_2$ gas stops after the discharge caused by the application of the HF current to the inert gas halts. Because the $CO_2$ gas serves to prevent unintended discharges occurring within the cap 402 and/or near the distal tip 201 of the endoscope device 200 until the discharge halts, the risk of damage to the distal tip 201 of the endoscope device 200 is diminished.

The control circuit may either execute Variation 3 or 4 after Variation 1 or execute Variation 3 or 4 after Variation 2.

FIG. 10 is a chart listing other various control sequences for commencing the ablation treatment procedure. The chart in FIG. 10 discloses different patterns of administrative control sequences (labeled as Seq. No. in FIG. 10) for controlling the endoscope device 200 and ablation treatment device 300 for commencing the ablation treatment procedure.

In sequence no. 1A, the $CO_2$ gas is injected during the 1st step, then the inert gas is injected during the 2nd step, and finally the HF current is applied during the 3rd step. During the 1st step, any remaining inert gas from previous procedures are pushed out from cap 402 and away from distal tip 201 by the injected $CO_2$ gas. The insert gas injected during the 2nd step accumulates near the ablation target area 404, while continuously injected $CO_2$ gas prevents the inert gas from accumulating inside or near cap 402 or distal tip 201. The HF current applied during the 3rd step will cause discharges to occur within the inert gas atmosphere 406 and ablate the ablation target area 404 without the concern of discharge occurring between electrode 302 and cap 402 or distal tip 201.

In sequence no. 2A, $CO_2$ gas is injected during the 1st step, then the HF current is applied during the 2nd step, and finally the inert gas is injected during the 3rd step. During the 1st step, any remaining inert gas from the previous procedures are pushed out from the cap 402 or distal tip 201 by the injected $CO_2$ gas. The HF current applied during the 2nd step will not create any discharge due to HF current being insufficient to ionize the injected $CO_2$ gas, but the HF current would be sufficient to create discharge between the electrode 302 and the ablation target area 404 after the insert gas atmosphere 406 is formed in the 3rd step, while continuously injected $CO_2$ gas prevents the inert gas from accumulating inside or near cap 402 or distal tip 201.

In sequence no. 3A, $CO_2$ gas is first injected during the 1st step, then the application of the HF current and injection of the inert gas occurs simultaneously during the 2nd step (no 3rd step for seq. no. 3A). During the 1st step, any remaining inert gas from the previous procedures are pushed out from the cap 402 or distal tip 201 by the injected $CO_2$ gas. The HF current applied and inert gas injected during the 2nd step will create discharges between the electrode 302 and the ablation target area 404 after the insert gas atmosphere 406 is formed, while continuously injected $CO_2$ gas prevents the inert gas from accumulating inside or near cap 402 or distal tip 201.

In sequence no. 4A, $CO_2$ gas and insert gas are simultaneously injected during the 1st step, then the application of the HF current occurs during the 2nd step (no 3rd step for seq. no. 4A). During the 1st step, any remaining inert gas from the previous procedures are pushed out from the cap 402 or distal tip 201 by the injected $CO_2$ gas, and inert gas atmosphere 406 is formed near the ablation target area 404. The HF current applied during the 2nd step will create discharges between the electrode 302 and the ablation target area 404, while continuously injected $CO_2$ gas prevents the inert gas from accumulating inside or near cap 402 or distal tip 201.

In sequence no. 5A, injection of $CO_2$ gas and application of HF current occurs simultaneously during the 1st step, then the injection of the insert gas occurs during the 2nd step (no 3rd step for seq. no. 5A). During the 1st step, any remaining inert gas from the previous procedures are pushed out from the cap 402 or distal tip 201 by the injected $CO_2$ gas, and application of the HF current does not create any discharges due to the $CO_2$ gas. The discharge between the electrode 302 and the ablation target area 404 will occur only after the insert gas atmosphere 406 is formed near the ablation target area 404 during the 2nd step, while continuously injected $CO_2$ gas prevents the inert gas from accumulating inside or near cap 402 or distal tip 201.

In sequence no. 6A, injection of $CO_2$ gas and insert gas, as well as the application of HF current occurs simultaneously during the 1st step (no 2nd or 3rd step for seq. no. 6A). During the 1st step, any remaining inert gas from the previous procedures are pushed out from the cap 402 or distal tip 201 by the injected $CO_2$ gas, while insert gas atmosphere 406 is formed near the ablation target area 404. The application of the HF current will create discharges between electrode 302 and the ablation target area 404 as soon as the insert gas atmosphere 406 is formed near the ablation target area 404, while continuously injected $CO_2$ gas prevents the inert gas from accumulating inside or near cap 402 or distal tip 201.

In sequence no. 7A, the inert gas is first injected towards the ablation target area 404 during the 1st step, then $CO_2$ gas is injected from the during the 2nd step, and then finally the HF current is applied during the 3rd step. During the 1st step, the injected insert gas forms the insert gas atmosphere 406 in the vicinity of the inner tube channel 304. The $CO_2$ gas injected during the 2nd step pushes out the accumulated inert gas and other dischargeable gas out from cap 402 and away from distal tip 201, while forming the inert gas atmosphere in the vicinity of the ablation target area 406. The HF current applied during the 3rd step will discharge and ablate the ablation target area 404 without the concern of discharge occurring between the electrode 302 and the cap 402 or distal tip 201.

In sequence no. 8A, the inert gas is injected during the 1st step, then the application of the HF current and injection of the $CO_2$ gas occurs simultaneously during the 2nd step (no 3rd step for seq. no. 8A). During the 1st step, the injected insert gas will form the insert gas atmosphere 406 near the inner tube channel 304. The HF current applied during the 2nd step will create a discharge between the electrode 302 and ablation target area 404, while the simultaneously injected $CO_2$ gas will prevent discharges from occurring between the electrode 302 and the cap 402 or distal tip 201.

In sequence no. 9A, the HF current is applied during the 1st step, the injection of the $CO_2$ gas occurs during the 2nd step, and the injection of the inert gas occurs during the 3rd step. During the 1st step, the applied HF current will not create discharges due to lack of insert gas atmosphere 406. During the 2nd step, the injected $CO_2$ gas pushes out and replaces any gas remaining in cap 402. Discharges may occur after the insert gas atmosphere 406 is created between the electrode 302 and ablation target area 404 during the 3rd step.

In sequence no. 10A, the HF current is applied during the 1st step, and the injection of the inert gas and $CO_2$ gas occurs during the 2nd step (no 3rd step for seq. no. 10A). During the 1st step, the applied HF current does not create discharges due to lack of insert gas atmosphere 406. During the 2nd step, discharges will occur after the insert gas atmosphere 406 is created between the electrode 302 and ablation target area 404, while the simultaneously injected $CO_2$ gas pushes out any gas remaining in cap 402 to prevent unintended discharges.

The common advantage for the sequences no. 1A to 10A is that the injection of the $CO_2$ gas occurs prior to or simultaneously with the HF current applied to the inert gas thereby causing a discharge. The injected $CO_2$ gas serves to prevent unintended discharges occurring within the cap 402 and/or near the distal tip 201 of the endoscope device 200.

FIG. 11 a chart listing further various control sequences for commencing the ablation treatment procedure. The chart in FIG. 11 discloses different patterns of administrative control sequences (labeled as Seq. No. in FIG. 11) for controlling the endoscope device 200 and ablation treatment device 300 for commencing the ablation treatment procedure.

In sequence no. 1B, the inert gas is injected during the 1st step, the HF current is applied during the 2nd step, and then the $CO_2$ gas is injected during the 3rd step. During the 1st step, the injected insert gas forms the insert gas atmosphere 406 near the inner tube channel 304. The HF current applied during the 2nd step will create a discharge between the electrode 302 and ablation target area 404. The $CO_2$ gas injected during the 3rd step will prevent discharges from occurring between the electrode 302 and the cap 402 or distal tip 201.

In sequence no. 2B, the injection of the inert gas and application of the HF current occurs simultaneously during the 1st step, then the injection of the $CO_2$ gas occurs during the 2nd step (no 3rd step for seq. no. 2B). During the 1st step, the injected insert gas will form the insert gas atmosphere 406 near the inner tube channel 304 and the simultaneously applied HF current will create a discharge between the electrode 302 and ablation target area 404. The $CO_2$ gas injected during the 2nd step will prevent discharges from occurring between the electrode 302 and the cap 402 or distal tip 201.

In sequence no. 3B, the HF current is applied during the 1st step, the injection of the inert gas occurs during the 2nd step, and the injection of the $CO_2$ gas occurs during the 3rd step. During the 1st step, the applied HF current will not create discharges due to lack of insert gas atmosphere 406. During the 2nd step, discharges may occur after the insert gas atmosphere 406 is created between the electrode 302 and ablation target area 404. The injected $CO_2$ gas pushes out any gas remaining in cap 402 other than the inert gas continuously injected through inner tube channel 306.

The common advantage for the sequences no. 1B to 3B is that the discharge may occur without waiting for the injection of the $CO_2$ gas, allowing immediate commencement of the treatment procedure that may also lead to shortening the time of the entire treatment procedure.

FIG. 12 is a chart listing other various control sequences for halting the ablation treatment procedure. The chart in FIG. 12 discloses different patterns of administrative control sequences (labeled as Seq. No. in FIG. 12) for controlling the endoscope device 200 and ablation treatment device 300 for halting the ablation treatment procedure.

In sequence no. 1C, the injection of $CO_2$ gas and inert gas are stopped during the 1st step, then the application of the HF current is stopped during the 2nd step (no 3rd step in seq. no. 1C). The discharge and the ablation procedure may halt after the $CO_2$ gas and inert gas are no longer injected as the insert gas atmosphere 406 is consumed or dissipates and no longer supports ionization. The discharge and the ablation procedure will halt during the 2nd step when the application of the HF current is turned off.

In sequence no. 2C, the injection of $CO_2$ gas and the application of the HF current are stopped during the 1st step, then the injection of the inert gas is stopped during the 2nd step (no 3rd step in seq. no. 2C). The discharge and the ablation procedure will halt during the 1st step when the application of the HF current is turned off.

In sequence no. 3C, the injection of $CO_2$ gas and inert gas, as well as the application of the HF current are all stopped during the 1st step (no 2nd or 3rd step in seq. no. 3C). The discharge and the ablation procedure will halt after all three activities are turned off.

In sequence no. 4C, the injection of the inert gas is stopped during the 1st step, then the injection of the $CO_2$ gas is stopped during the 2nd step, and then the application of the HF current is stopped during the 3rd step. The discharge and the ablation procedure will halt during the 1st step when the injection of the inert gas is stopped, since the insert gas atmosphere 406 between electrode 302 and ablation target area 404 will be pushed out by the continued injection of the $CO_2$ gas.

In sequence no. 5C, the injection of the inert gas is stopped during the 1st step, then the application of the HF current is stopped during the 2nd step, and then the injection of the $CO_2$ gas is stopped during the 3rd step. The discharge and the ablation procedure will halt during the 1st step when the injection of the inert gas is stopped, since the insert gas atmosphere 406 between electrode 302 and ablation target area 404 will be pushed out by the continued injection of the $CO_2$ gas.

In sequence no. 6C, the injection of the inert gas is stopped during the 1st step, then the application of the HF current and the injection of the $CO_2$ gas are stopped during the 2nd step (no 3rd step in seq. no. 6C). The discharge and the ablation procedure will halt during the 1st step when the injection of the inert gas is stopped, since the insert gas atmosphere 406 between electrode 302 and ablation target area 404 will be pushed out by the continued injection of the $CO_2$ gas.

In sequence no. 7C, the injection of the inert gas and application of the HF current is stopped during the 1st step, then the injection of the $CO_2$ gas is stopped during the 2nd step (no 3rd step in seq. no. 7C). The discharge and the ablation procedure will halt during the 1st step after the injection of the inert gas and the application of the HF current are stopped.

In sequence no. 8C, the application of the HF current is stopped during the 1st step, then the injection of the $CO_2$ gas is stopped during the 2nd step, and the injection of the inert gas is stopped during the 3rd step. The discharge and the ablation procedure will halt during the 1st step after the application of the HF current is stopped.

In sequence no. 9C, the application of the HF current is stopped during the 1st step, then the injection of the inert gas is stopped during the 2nd step, and the injection of the $CO_2$ gas is stopped during the 3rd step. The discharge and the ablation procedure will halt during the 1st step after the application of the HF current is stopped.

In sequence no. 10C, the application of the HF current is stopped during the 1st step, then the injection of the inert gas and $CO_2$ gas are stopped during the 2nd step (no 3rd step in seq. no. 10C). The discharge and the ablation procedure will halt during the 1st step after the application of the HF current is stopped.

The common advantage for the sequences no. 1C to 10C is that the injection of the $CO_2$ gas stops after the discharge caused by the application of the HF current to the inert gas halts. Because the $CO_2$ gas serves to prevent unintended discharges occurring within the cap 402 and/or near the distal tip 201 of the endoscope device 200 until the discharge halts, the risk of damage to the distal tip 201 of the endoscope device 200 is diminished.

FIG. 13 is a chart listing further various control sequences for halting the ablation treatment procedure. The chart in FIG. 13 discloses a chart describing different patterns of administrative control sequences (labeled as Seq. No. in FIG. 13) for controlling the endoscope device 200 and ablation treatment device 300 for halting the ablation treatment procedure.

In sequence no. 1D, the injection of $CO_2$ gas is stopped during the 1st step, then the injection of the inert gas is stopped during the 2nd step, and then the application of the HF current is stopped during the 3rd step. The discharge and the ablation procedure continue after the $CO_2$ gas is no longer injected during the 1st step, but may halt during the 2nd step when the inert gas is no longer injected and the insert gas atmosphere 406 is consumed or dissipates and no longer supports ionization. Even if the discharge and the ablation procedure continue through the 2nd step, it will halt during the 3rd step when the application of the HF current is turned off.

In sequence no. 2D, the injection of $CO_2$ gas is stopped during the 1st step, then the application of the HF current is stopped during the 2nd step, and then the injection of the inert gas is stopped during the 3rd step. The discharge and the ablation procedure continue after the $CO_2$ gas is no longer injected during the 1st step, but will halt during the 2nd step when the application of the HF current is turned off.

In sequence no. 3D, the injection of $CO_2$ gas is stopped during the 1st step, then the application of the HF current and injection of the inert gas are stopped during the 2nd step (no 3rd step in seq. no. 3D). The discharge and the ablation procedure continue after the $CO_2$ gas is no longer injected during the 1st step, but will halt during the 2nd step when the application of the HF current and the injection of the inert gas is turned off.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:

1. An endoscope system, comprising:

an endoscope including an insertion channel;

a treatment tube inserted through and protruding out from a distal end of the insertion channel, wherein the treatment tube includes an electrode and a first gas channel;

a first gas source configured to supply a first gas at a first flow rate through the first gas channel;

a second gas source configured to supply a second gas at a second flow rate through a second gas channel, wherein the second gas channel is the insertion channel and supplies the second gas from the distal end of the insertion channel; and a control circuit controlling the first gas source and the second gas source, wherein the control circuit is configured to send a control signal to the first gas source and the second gas source so that the second flow rate is larger than the first flow rate when both of the first gas and the second gas are supplied.

2. The endoscope system as in claim 1, wherein the second gas is carbon dioxide.

3. The endoscope system according to claim 1, wherein the first gas is Argon and the second gas is carbon dioxide, and wherein a first high frequency current applied to the electrode is sufficient to ionize Argon into the plasma state but not sufficient to ionize the carbon dioxide into the plasma state.

4. The endoscope system according to claim 1, wherein a plenum between an outer surface of a wall of the electrode and an inner surface of the wall of the treatment tube forms the first gas channel.

5. The endoscope system according to claim 1, wherein a plenum between an outer surface of a wall of the treatment tube and an inner surface of the wall of the insertion channel forms the second gas channel.

6. The endoscope system according to claim 1, wherein the second gas channel is formed within the endoscope and is separate from the insertion channel, and wherein the second gas channel has an opening in a distal end of the endoscope that is spaced apart from an opening for the treatment tube in the distal end of the endoscope.

7. The endoscope system according to claim 1, further comprising:

an electricity power source configured to supply a first high frequency current to the electrode sufficient to ionize the first gas into a plasma state.

8. The endoscope system according to claim 7, wherein the control circuit is programmed to supply the second gas prior to or simultaneously with supplying the first gas or supply the second gas prior to or simultaneously with applying the first high frequency current to the electrode.

9. The endoscope system according to claim 7, wherein the control circuit is programmed to supply the second gas after supplying the first gas and the applying of the first high frequency current to the electrode.

10. The endoscope system according to claim 7, wherein the control circuit is programmed to stop the supply of the second gas prior to stopping the supply of the first gas or stopping the application of the first high frequency current.

11. The endoscope system according to claim 7, wherein the control circuit is programmed to stop the supply of the second gas after stopping the supply of the first gas or stopping the application of the first high frequency current.

12. A control device for an endoscope, comprising:

a controller including a control circuit for controlling a first gas source, and a second gas source, wherein the first gas source is configured to supply a first gas through a first gas channel from a treatment tool inserted into the endoscope, wherein the second gas source is configured to supply a second gas through a second gas channel, wherein the second gas channel is the insertion channel of the endoscope and supplies the second gas from a distal end of the insertion channel, wherein a flow rate of the first gas is a first flow rate and a flow rate of the second gas is a second flow rate, and wherein the control circuit is configured to send a control signal to the first gas source and the second gas source so that the second flow rate is larger than the first flow rate when both of the first gas and the second gas are supplied.

13. The control device as in claim 12, wherein the control circuit is programmed to supply the second gas prior to or simultaneously with supplying the first gas or supply the second gas prior to or simultaneously with applying a first high frequency current to an electrode of the endoscope.

14. The control device as in claim 12, wherein the control circuit is programmed to supply the second gas after supplying the first gas and applying a first high frequency current to an electrode of the endoscope.

15. The control device as in claim 13, wherein the control circuit is programmed to stop the supply of the second gas prior to stopping the supply of the first gas or stopping the application of the first high frequency current.

16. The control device as in claim 13, wherein the control circuit is programmed to stop the supply of the second gas after stopping the supply of the first gas or stopping the application of the first high frequency current.

17. A method of controlling a flow of a first gas and a second gas in an endoscope, a first gas source configured to supply the first gas through a first gas channel in a treatment tube located in an insertion channel of the endoscope, and a second gas source configured to supply the second gas through a second gas channel in the endoscope, the method comprising:

supplying the first gas at a first flow rate through the first gas channel aimed to reach beyond a distal end of an electrode; and supplying the second gas at a second flow rate through the second gas channel not aimed to reach beyond the distal end of an electrode included in the treatment tube, wherein the second gas channel is the insertion channel and supplies the second gas from a distal end of the insertion channel, wherein the second flow rate is larger than the first flow rate when both of the first gas and the second gas are supplied.

18. The method as in claim 17, wherein the second gas is supplied prior to or simultaneously with supplying the first gas or the second gas is supplied prior to or simultaneously with applying a first high frequency current to an electrode of the endoscope.

19. The method as in claim 17, the second gas is supplied after supplying the first gas and applying a first high frequency current to an electrode of the endoscope.

20. The method as in claim 18, wherein the supply of the second gas is stopped prior to stopping the supply of the first gas or stopping the application of the first high frequency current.

21. The method as in claim 18, wherein the supply of the second gas is stopped after stopping the supply of the first gas or stopping the application of the first high frequency current.

22. The endoscope system according to claim 7, wherein the first gas ionizes into the plasma state at the first high frequency amperage, the second gas ionizes into a plasma state at a second high frequency amperage, and the second high frequency current is higher than the first high frequency amperage.

23. The endoscope system according to claim 1, further comprising:

a cap attached to an outer surface of the endoscope, a distal end of the cap located distally relative to a distal end of the endoscope, wherein the second gas is discharged only from a distal opening of the cap toward an outside of the cap, and wherein the first gas is discharged only from a distal opening of the treatment tube toward outside of the cap.

24. The control device as in claim 12, wherein the control circuit further controls an electricity power source, and wherein the electricity power source is configured to supply a first high frequency current to an electrode located in a treatment tube of the endoscope that is sufficient to ionize the first gas into a plasma state.

25. The control device as in claim 24, wherein the first gas ionizes into the plasma state at the first high frequency amperage, the second gas ionizes into a plasma state at a second high frequency amperage, and the second high frequency current is higher than the first high frequency amperage.

26. The method as in claim 17, further comprising applying a first high frequency current to an electrode to ionize the first gas to a plasma state, wherein the first high frequency current is sufficient to ionize the first gas into a plasma state, and wherein the first gas ionizes into the plasma state at the first high frequency current, the second gas ionizes into a plasma state at a second high frequency current, and the second high frequency current is higher than the first high frequency current.

27. The endoscope system as in claim 1, wherein the control circuit is configured to:

supply the first gas, and supply the second gas before the electrode is activated, wherein the first gas is inert gas, and wherein the second gas is other than inert gas.

28. The method as in claim 17, wherein the first gas is inert gas, and wherein the second gas is other than inert gas.

* * * * *